United States Patent
Nakamura et al.

(10) Patent No.: US 6,379,910 B1
(45) Date of Patent: Apr. 30, 2002

(54) MEASURING APPARATUS AND METHOD FOR MATERIAL OR ORGANISM INDUCING PH-CHANGE OF SUBSTRATE SOLUTION

(75) Inventors: Michihiro Nakamura; Harutoshi Terasawa; Hiroyuki Okada; Hidenori Yukawa; Hidehiro Hosaka, all of Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 09/090,410

(22) Filed: Jun. 4, 1998

(30) Foreign Application Priority Data

Jun. 5, 1997 (JP) ................................ 9-147444

(51) Int. Cl.[7] ................................. C12Q 1/58
(52) U.S. Cl. .................. 435/12; 435/7.1; 435/7.32; 436/512; 436/501; 422/61; 422/57; 422/81
(58) Field of Search ................. 435/7.32, 7.1, 435/12; 436/512, 501; 422/61, 57, 81

(56) References Cited

U.S. PATENT DOCUMENTS

| | | | |
|---|---|---|---|
| 4,398,554 A | * | 8/1983 | Kondo |
| 4,568,444 A | * | 2/1986 | Nakamura |
| 4,585,623 A | * | 4/1986 | Chandler |
| 4,659,678 A | * | 4/1987 | Forrest et al. |
| 4,690,801 A | * | 9/1987 | Anderson |
| 4,778,769 A |   | 10/1988 | Forrest et al. |
| 4,810,658 A | * | 3/1989 | Shanks et al. |
| 5,066,582 A |   | 11/1991 | Tsuruta et al. |
| 5,077,197 A | * | 12/1991 | Forrest et al. |
| 5,120,648 A | * | 6/1992 | Lim et al. |
| 5,133,937 A | * | 7/1992 | Frackleton et al. |
| 5,158,868 A |   | 10/1992 | Bergkuist et al. |
| 5,253,539 A | * | 10/1993 | Maciel et al. |
| 5,319,226 A | * | 6/1994 | Sohn et al. |
| 5,556,760 A | * | 9/1996 | Nakamura et al. |
| 5,674,696 A |   | 10/1997 | Nakamura et al. |

FOREIGN PATENT DOCUMENTS

| | | |
|---|---|---|
| EP | 0 329 458 | 8/1989 |
| EP | 0 651 251 | 5/1995 |
| EP | 0 685 199 | 12/1995 |
| WO | WO 89/05977 | 6/1989 |

* cited by examiner

*Primary Examiner*—Mark Navarro
*Assistant Examiner*—Ginny Allen Portner
(74) *Attorney, Agent, or Firm*—Sughrue Mion, PLLC (57) ABSTRACT

One end of a thin-tube type solid phase in which a receptor specific for a material or an organism to be measured which can induce a pH-change of substrate solution is immobilized is soaked in a sample solution and then taken out therefrom. The one end of the thin-tube type solid phase is disposed in a measurement cell and a sensing portion of a pH electrode disposed in the measurement cell is in the vicinity of the one end of the thin-tube type solid phase. The measurement cell and the thin-tube type solid phase are filled with a substrate solution so that a reaction takes place. Thereafter, the substrate solution in the thin-tube type solid phase is moved to the sensing portion by a solution feed pump. The output of the pH electrode at this timing is detected.

9 Claims, 5 Drawing Sheets

MEASURING APPARATUS AND METHOD FOR MATERIAL OR ORGANISM INDUCING PH-CHANGE OF SUBSTRATE SOLUTION

BACKGROUND OF THE INVENTION

1. Field of the Invention

The invention relates to an apparatus and a method for, in a diagnosis, a food inspection, or the like, measuring a material (for example, an enzyme) or an organism (for example, a cell or a microorganism) which decomposes a substrate in a solution and induces a pH-change of the solution.

2. Related Art

In the fields of medicine and food, it is requested to specifically and rapidly make a measurement on a trace amount of a material or an organism which can induce a pH-change of substrate solution. A material or an organism which can induce a pH-change of substrate solution can be detected by using a pH electrode. Generally, it cannot be insisted that a measurement using a pH electrode is sufficiently high in specificity and sensitivity. In order to improve this point, recently, an apparatus has been disclosed in which the specific molecular reconizability of an antibody and features of a minute pH electrode are utilized so as to perform a highly sensitive and rapid measurement (U.S. Pat. No. 5,674,696 and U.S. Pat. No. 5,066,582).

Figure 4:
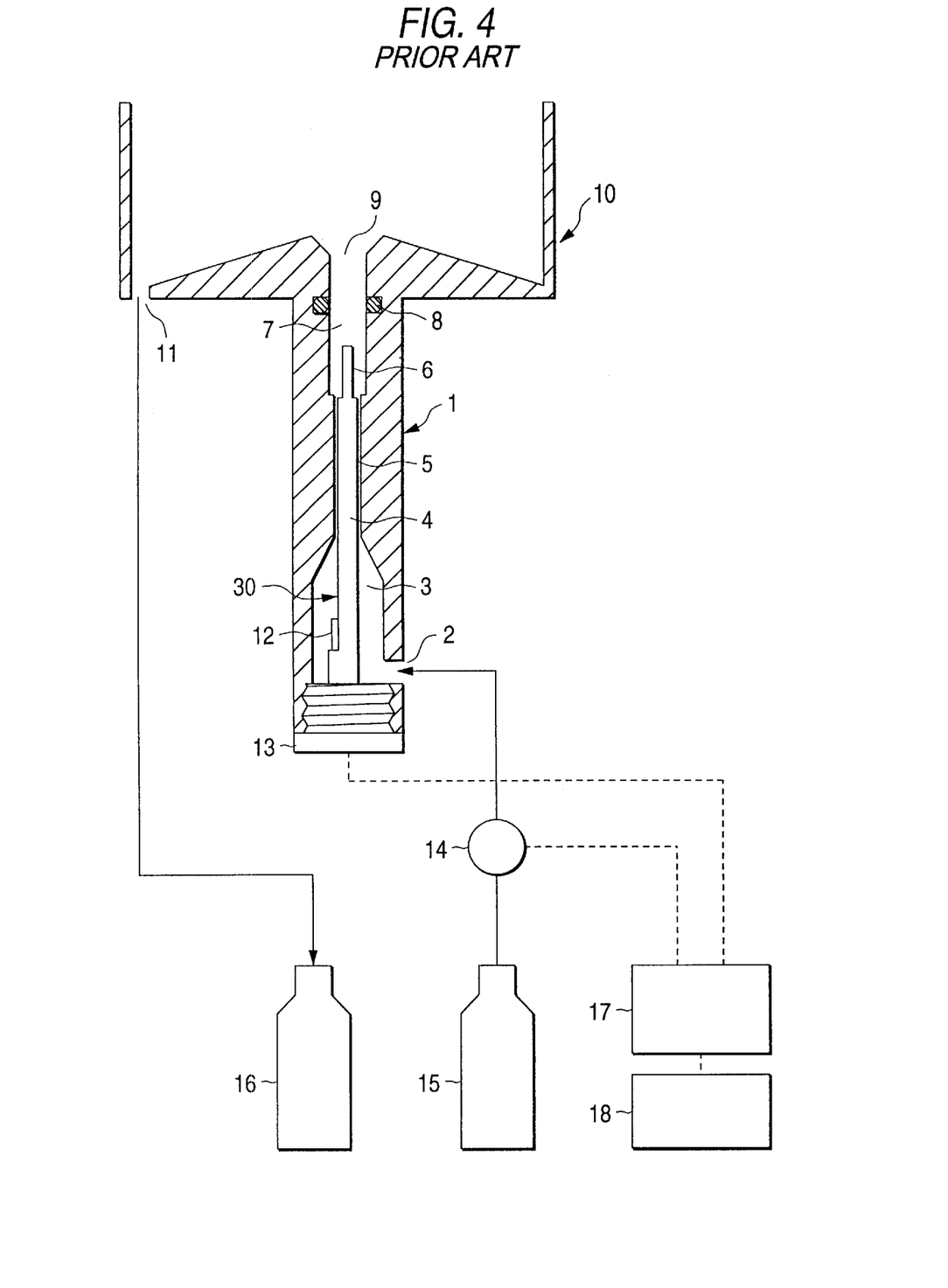
FIG. 4 is a diagram showing a measuring apparatus of the prior art.
Figure 5:
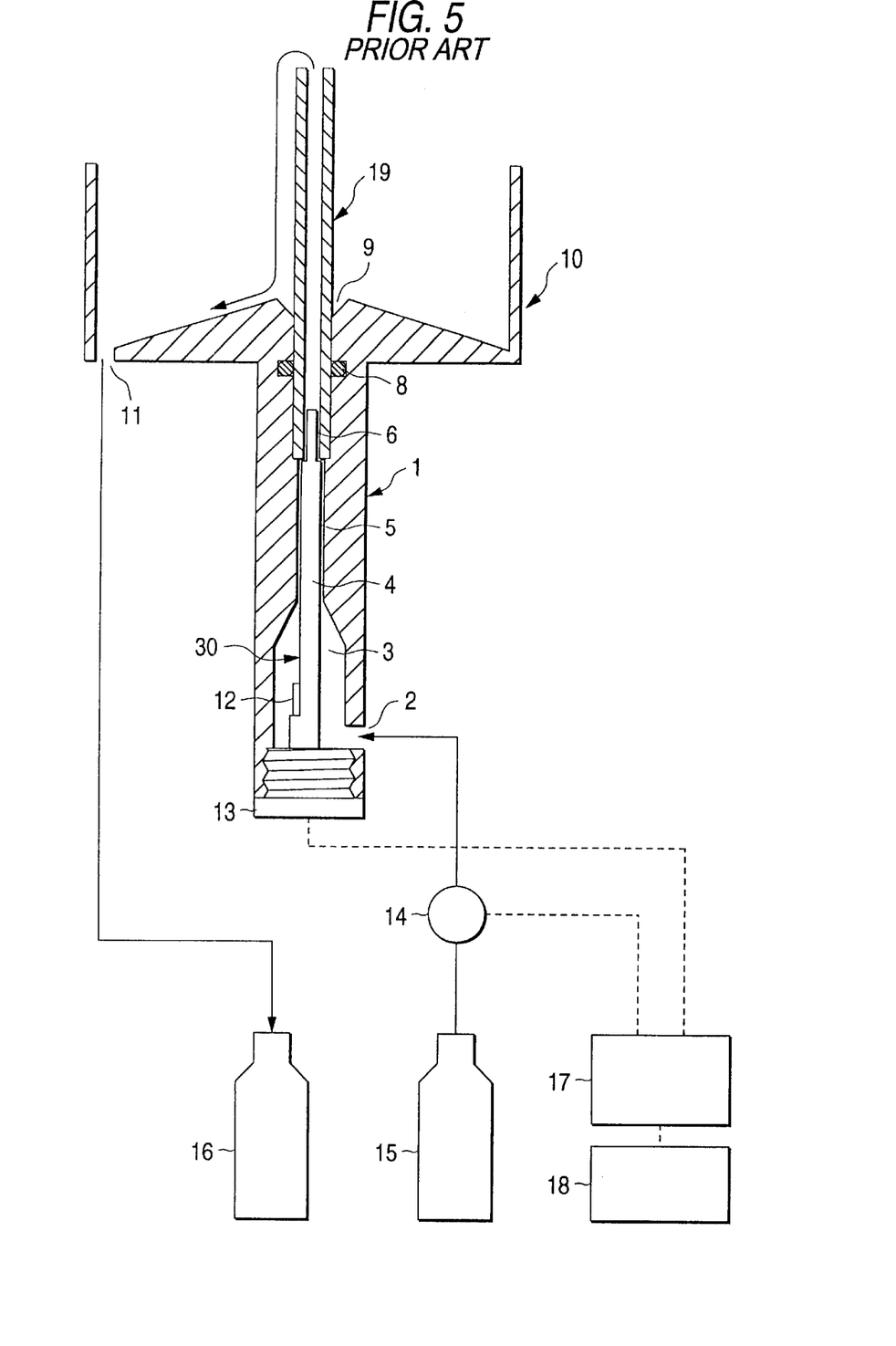
FIG. 5 is a diagram illustrating a measurement using the apparatus shown in FIG. 4.

FIG. 4 shows the apparatus, and FIG. 5 shows a state in which the apparatus is used. Portions of the apparatus will be described. A measurement cell 1 has a cylindrical shape in which an opening is formed at each of the upper and lower ends. A through hole is formed in the peripheral wall in the vicinity of the lower end and functions as a substrate solution inlet 2. The interior of the measurement cell 1 is composed, in the sequence starting from the lower end, of a portion filled with fresh substrate solution 3 of a large diameter, a pH electrode body accommodating portion 5 of a small diameter, and a thin-tube type solid phase insertion portion 7 which is slightly larger in diameter than the pH electrode body accommodating portion 5. A pH electrode 30 is inserted into the whole of the interior of the measurement cell. A pH electrode body portion 4 of the pH electrode 30 is accommodated in the portion filled with fresh substrate solution 3 and the pH electrode body accommodating portion 5. A pH electrode sensing portion 6 of the pH electrode 30 is accommodated in the thin-tube type solid phase insertion portion 7. A pH electrode connector 13 is attached to the basal end of the pH electrode 30. The opening of the lower end of the measurement cell 1 is hermetically sealed by the pH electrode connector 13. A reference electrode 12 is attached to the pH electrode connector 13 so as to be accommodated in the portion filled with fresh substrate solution 3.

An annular groove is formed in the peripheral wall of the thin-tube type solid phase insertion portion 7 of the measurement cell 1. An O-ring 8 is fitted into the groove. The O-ring 8 is used for, when a thin-tube type solid phase 19 shown in FIG. 5 is inserted into the thin-tube type solid phase insertion portion 7, hermetically sealing a gap between the thin-tube type solid phase 19 and the peripheral wall of the thin-tube type solid phase insertion portion 7.

The upper end opening of the measurement cell 1 serves as a thin-tube type solid phase insertion port 9 through which the thin-tube type solid phase 19 shown in FIG. 5 is to be inserted into the thin-tube type solid phase insertion portion 7. The outside of the upper end of the measurement cell 1 is a substrate solution overflow portion 10 from which an overflowing substrate solution is recovered. The substrate solution which is recovered from the substrate solution overflow portion 10 reaches a waste solution vessel 16 via a substrate solution outlet 11.

By contrast, the supply of the substrate solution to the measurement cell 1 is performed by supplying a substrate solution contained in a substrate solution vessel 15, by a solution feed pump 14 via the substrate solution inlet 2.

An electric circuit unit 17 has a data processing function which performs calculations on the basis of electric signals from the pH electrode 30 and the reference electrode 12, to calculate a pH-change and supplies the calculation result to a display unit, and a drive controlling function which controls the driving of the solution feed pump 14.

The display unit 18 performs a display corresponding to the signal supplied from the electric circuit unit 17.

When urease secreted by Helicobacter pylori is to be detected by the thus configured apparatus, for example, a monoclonal antibody to urease secreted by Helicobacter pylori serving as a receptor is previously fixed to the inner and outer walls of the thin-tube type solid phase 19.

The operator then soaks one end portion of the thin-tube type solid phase 19 in a sample solution for a given time period and takes out it from the sample solution. The one end portion is accommodated in the thin-tube type solid phase insertion portion 7 through the thin-tube type solid phase insertion port 9 of the measurement cell 1. As a result, as shown in FIG. 5, a so-called coupling state in which the pH electrode sensing portion 6 is inserted into the thin-tube type solid phase 19 is established. Under this state, the operator instructs the electric circuit unit 17 to start the operation, so that the solution feed pump 14 is driven and the substrate solution is supplied to the interior of the thin-tube type solid phase 19 to wash the interior. After a predetermined time period elapses, the solution feed pump 14 is stopped and there occurs a pH-change in the substrate solution in the thin-tube type solid phase 19. The electric circuit unit 17 detects the change on the basis of the output voltage of the pH electrode 30, and the value of the detected change is displayed on the display unit 18.

However, it has been noted that there arise the following problems in such an apparatus when the thin tube of the thin-tube type solid phase 19 is coupled with the pH electrode sensing portion 6 of the pH electrode 30.

(1) In the apparatus, in order to improve the detection sensitivity and the detection speed, the distance between the inner wall of the thin tube and the sensing portion of the pH electrode must be as short as possible, and hence the inner diameters of the thin tube and the sensing portion of the pH electrode are required to be as thin as possible. However, it is difficult to produce such a thin tube and a pH electrode. Particularly, there is a limitation in the thinness of the sensing portion of a pH electrode. When a pH sensitive field effect transistor (hereinafter, referred to as "pH-FET") is used as a pH electrode, for example, the sensing portion practically has a diameter of about 0.5 mm. In accordance with this diameter, the inner diameter of a thin tube can be made to be about 0.6 mm. When a thin tube has a diameter smaller than this value, it is impossible to achieve the above-mentioned coupling.

(2) In a method in which a thin tube is coupled with a pH electrode, when the thin tube has an error in dimension or shape, there is a fear that the thin tube is contacted with the pH electrode so that the pH electrode is damaged or contaminated.

SUMMARY OF THE INVENTION

It is an object of the invention to achieve a measurement which is excellent in detection sensitivity and detection speed, and also a measurement which can be performed without causing a thin tube and the sensing portion of a pH electrode to be contacted with each other.

The apparatus for measuring material which induce a pH-change of substrate solution comprises: a thin-tube type solid phase comprising a thin tube, a receptor specific for the material which can induce a pH-change of substrate solution or the organism which can induce a pH-change of substrate solution being immobilized at least to an interior of said thin tube, the material or the organism being a measuring object; a measuring cell which accommodates a substrate solution containing a substrate for the material which can induce a pH-change of substrate solution or the organism which can induce a pH-change of substrate solution; thin-tube type solid phase holding means for holding at least one end of said thin-tube type solid phase, in said cell; a pH electrode having a sensing portion which is disposed in the vicinity of said one end of said thin-tube type solid phase held in said cell, said pH electrode detecting a pH change of said substrate solution; and substrate solution moving means for moving said substrate solution in said thin-tube type solid phase held in said cell, toward said sensing portion.

When a material which can induce a pH-change of substrate solution or an organism which can induce a pH-change of substrate solution is to be measured by using the apparatus, the operator soaks one end of the thin-tube type solid phase in the sample solution. The thin-tube type solid phase is then held in the cell by the holding means. When the substrate solution is accommodated in the cell, a pH-change occurs in the substrate solution in the thin-tube type solid phase. Thereafter, the substrate solution in the thin-tube type solid phase is moved to the sensing portion of the pH electrode by the substrate solution moving means. The pH electrode detects the pH of the substrate solution at this timing.

According the apparatus for measuring material which induce a pH-change of substrate solution, in said cell, a volume of a space between a basal end of said sensing portion of said pH electrode and said one end of said thin-tube type solid phase excluding a volume occupied by said sensing portion is 10 microliters or less. When the portion has a volume of such a degree, the substrate solution can reach the sensing portion of the pH electrode without being substantially diluted.

According to the apparatus for measuring material which induce a pH-change of substrate solution, said receptor is an antibody to urease secreted by Helicobacter pylori, and said substrate solution is a solution containing urea. According to the apparatus, it is possible to measure the concentration of urease secreted by Helicobacter pylori.

According to the apparatus for measuring material which induce a pH-change of substrate solution, said pH electrode is a pH sensitive field effect transistor. The apparatus is small in size. A measurement using the apparatus can be performed with a high sensitivity and a high speed.

According to the apparatus for measuring material which induce a pH-change of substrate solution, said thin-tube type solid phase has a fibrous material in which the receptor specific to a material which can induce a pH-change of substrate solution or an organism which can induce a pH-change of substrate solution is immobilized to the interior of said thin tube, the material or the organism being a measuring object. In the apparatus, the specific surface area of the solid phase can be increased as compared with the case using a simple thin tube, whereby the detection limit for a material or an organism to be measured can be lowered.

According to the apparatus for measuring material which induce a pH-change of substrate solution, one end of a thin-tube type solid phase comprising a thin tube is soaked in a sample solution and then taken out from said sample solution, a receptor specific for a material which can induce a pH-change of substrate solution or an organism which can induce a pH-change of substrate solution being immobilized at least to an interior of said thin tube, the material or the organism being a measuring object; said one end of said thin-tube type solid phase is disposed in a substrate solution and in the vicinity of a sensing portion of a pH electrode detecting a pH-change of a solution, said substrate solution containing a substrate for the material which can induce a pH-change of substrate solution or the organism which can induce a pH-change of substrate solution; and said substrate solution in said thin-tube type solid phase after a reaction of induction of a pH-change is moved to said sensing portion of said pH electrode.

In the method, the pH electrode outputs a result which is identical with that measured by inserting a sensing portion into a thin-tube type solid phase.

DETAILED DESCRIPTION OF THE PREFERRED EMBODIMENTS

Figure 1:
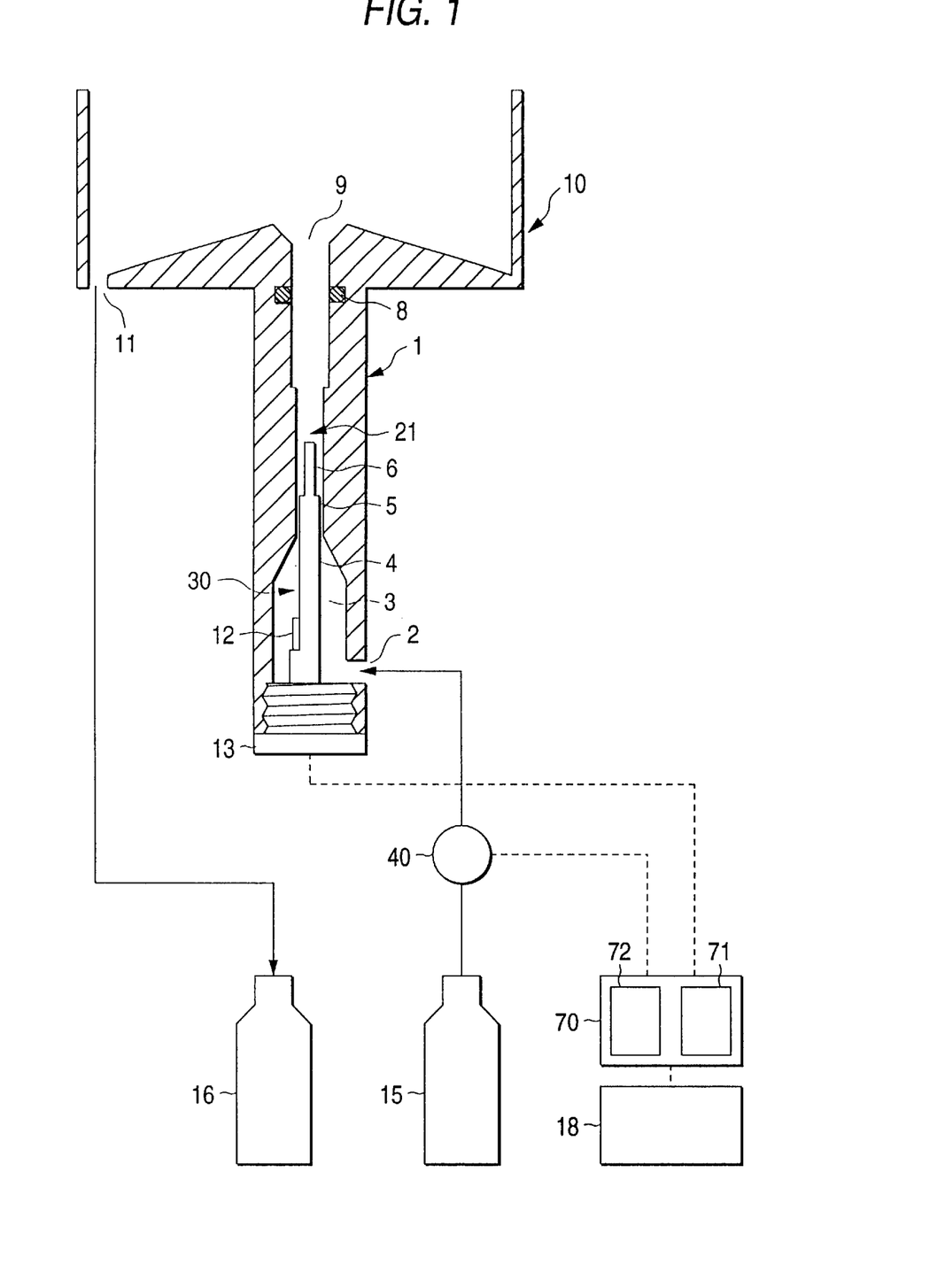
FIG. 1 is a diagram showing the configuration of an apparatus of an embodiment of the invention.
Figure 2:
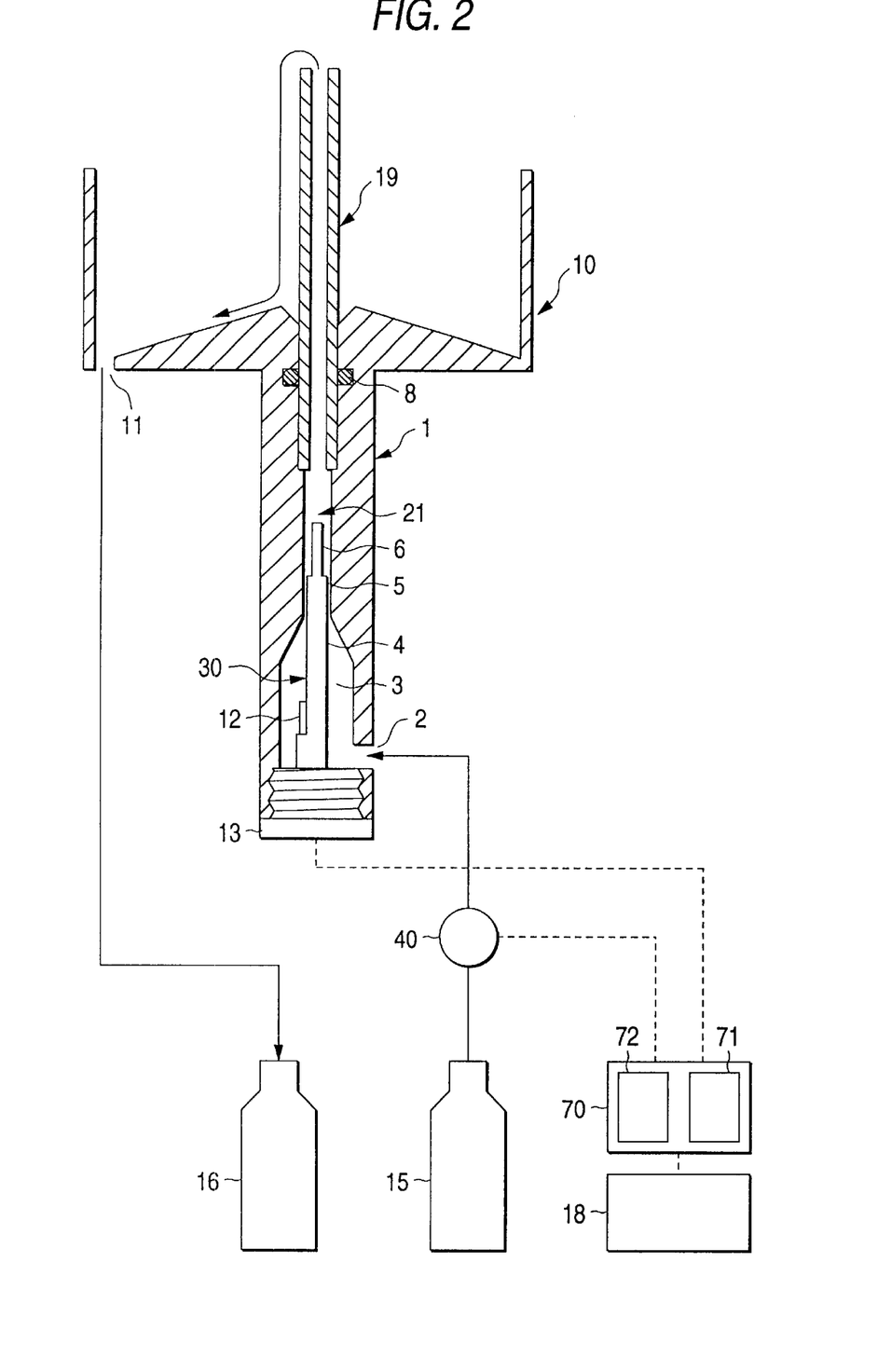
FIG. 2 is a diagram illustrating a measurement using the apparatus shown in FIG. 1.

FIG. 1 shows the configuration of the apparatus, and FIG. 2 shows a state in which the apparatus is used. The apparatus is different from that of the prior art shown in FIGS. 4 and 5 in that a pH electrode sensing portion accommodating portion 21 is disposed between the pH electrode body accommodating portion 5 and thin-tube type solid phase insertion portion 7 in the measurement cell 1 of the prior art apparatus. The pH electrode sensing portion 6 is accommodated in the pH electrode sensing portion accommodating portion. In the prior art apparatus, the solution feed pump 14 supplies the substrate solution to the measurement cell 1 in a one-way manner. By contrast, in the embodiment, a solution feed pump 40 operates also so as to suck the substrate solution in the measurement cell 1 although the sucking amount is very smaller than the supplying amount of the substrate solution. Therefore, an electric circuit unit 70 is configured in a slightly different manner from the electric circuit unit 17 of the prior art apparatus, so that the solution feed pump 40 can rotate in both the forward and rearward directions. The other portions are configured in the same manner as those of the prior art apparatus and hence designated by the same reference numerals. Hereinafter, the main portions will be described in detail.

(1) Measurement cell 1: for example, the measurement cell 1 is made of plastic, a metal, or glass.

(2) pH Electrode 30: a usual glass electrode, a pH-FET, or the like is used. A pH-FET has features such as that it can be easily miniaturized, that it is rapid in response to a pH-change, and that temporal changes of the properties such as the pH sensitivity are small in degree. Therefore, a pH-FET is most suitable for the apparatus of the embodiment.

(3) pH electrode sensing portion accommodating portion 21: this portion accommodates the pH electrode sensing portion 6. After a reaction of induction of a pH-change, the substrate solution in the thin-tube type solid phase 19 is reversely flown into the portion so as to fill the portion. In order to minimize the dilution effect in this case, it is preferable to reduce the death volume of the portion (the difference between the volume of the pH electrode sensing portion accommodating portion 21 and that of the portion of the pH electrode accommodated in the accommodating portion, i.e., that of the pH electrode sensing portion 6). When the death volume of the portion is reduced in this way, the amount of a reverse flow can be reduced and the volume of the whole of the measurement cell can be reduced, thereby attaining an effect that the required amount of the sample solution can be made smaller. Preferably, the death volume is 10 microliters or less.

(4) Thin-tube type solid phase insertion portion 7: one end portion of the thin-tube type solid phase 19 is to be inserted into the portion. When the thin-tube type solid phase 19 is inserted, the O-ring 8 hermetically seals the gap between the thin-tube type solid phase 19 and the peripheral wall of the thin-tube type solid phase insertion portion 7. Therefore, the substrate solution flows only through the interior of the thin-tube type solid phase 19 and does not flow into the outer peripheral region of the thin-tube type solid phase 19. When the thin-tube type solid phase 19 is inserted, the pH electrode sensing portion 6 is located outside the tip end of the thin-tube type solid phase. The thin-tube type solid phase insertion portion 7 and the O-ring 8 constitute the thin-tube type solid phase holding means.

(5) Reference electrode 12: the electrode is disposed in the portion filled with fresh substrate solution 3. A liquid-junction type reference electrode such as a saturated calomel electrode or an Ag/AgCl electrode is used as the reference electrode. Alternatively, a reference pH-FET and a pseudo reference electrode (a silver wire or the like) may be disposed in the portion, and the difference between the output voltages of the reference pH-FET and the measurement pH-FET may be measured.

(6) Solution feed pump 40: a pump which can rotate in both the forward and rearward directions. In order to supply a correct amount of the solution, preferably, a stepping motor is used in the pump. The reverse flow function of the solution feed pump 40 corresponds to the substrate solution moving means.

(7) Thin-tube type solid phase 19: as the material of the thin tube, for example, polyethylene, polypropylene, polystyrene, or the like is used. The thin-tube type solid phase 19 can be produced by immobilizing a receptor for a material to be measured or an organism to be measured at least onto the inner wall face of the thin tube. As the receptor, useful are an antibody, a binding protein for a specific protein (including receptors), the cell adhesion factor, etc.

These receptors are immobilized to the thin tube by a method similar to that used in the preparation of the solid phase in the enzyme immuno assay. Most usually, the preparation is conducted by physically adsorbing a receptor to the thin tube, and then blocking by bovine serum albumin or the like.

When the inner radius of the thin tube is indicated by r and the length by l, the specific surface area s of the inner wall to the volume of the interior of the thin tube is inversely proportional to the inner diameter r of the thin tube as follows:

$$s=(2\pi r l)/(\pi r^2 l)=2/r$$

In other words, as the inner diameter r of the thin tube is smaller, the specific surface area s is larger, and the speed of the reaction of induction of a pH-change is faster. Therefore, it is preferable to set the inner diameter r of the thin tube to be as small as possible. Usually, it is preferable to set the inner diameter r to be 1 mm or less. In a practical case, however, it is difficult to set the inner diameter r to be 1 mm or less, because of the moldability in the molding of the thin tube by using dies, the operability in the immobilization of the receptor to the thin tube, and the like.

In the apparatus, alternatively, the thin-tube type solid phase may be produced, in place of the coupling of the thin tube with the pH electrode, by, for example, filling the interior of the thin tube with glass fibers or synthetic fibers to which a receptor is previously immobilized. In the alternative, the fibers have a large specific surface area, and hence the inner diameter of the thin tube may be 1 mm or larger.

(8) Substrate solution: the substrate solution used in the apparatus means a solution containing a compound (substrate) which is decomposed or metabolized by a material which can induce a pH-change of substrate solution or by an organism which can induce a pH-change of substrate solution, to induce a pH-change. When the material to be measured is an enzyme, materials such as urease/urea, glucose oxidase/glucose, and lipase/triacylglycerol may be used as the substrate.

When the material to be measured is an organism such as a cell or a microorganism, an aqueous solution containing a substrate which is metabolized by such an organism to induce a pH-change may be used as the substrate solution. Most usually, saccharides such as glucose, fructose, and saccharose are used as such a substrate.

(9) Electric circuit unit 70: the unit comprises: a data processing unit 71 which performs calculations on the basis of electric signals from the pH electrode 30 and the reference electrode 12, to calculate a pH-change and supplies the calculation result to a display unit; and a drive controlling unit 72 which controls the driving of the solution feed pump 40.

Next, a method of measuring the concentration of a material to be measured or an organism to be measured in a sample solution by using the thus configured apparatus will be described.

First, the operator soaks one end portion of the thin-tube type solid phase 19 in the sample solution so that the sample solution is sucked into the thin tube. When the diameter of the thin tube is 1 mm or less, the sample solution is naturally sucked by the capillary phenomenon into the thin tube without intentionally performing a sucking operation. When the thin tube is allowed to stand under this state for a given time period, the material which can induce a pH-change of substrate solution or the organism which can induce a pH-change of substrate solution, which is in the sample solution, and which is to be measured is captured by the receptor in the thin tube.

Next, the operator inserts the one end portion of the thin-tube type solid phase 19 which has undergone the above-mentioned operation, into the thin-tube type solid phase insertion portion 7 through the thin-tube type solid phase insertion port 9 of the measurement cell 1. The state at this time is shown in FIG. 2. Thereafter, the operator instructs the electric circuit unit 70 to start the operation, so that the solution feed pump 40 is driven and the substrate solution accommodated in substrate solution vessel 15 is supplied to the measurement cell 1, thereby sufficiently washing the interior of the thin-tube type solid phase 19. As a result of this operation, a material to be measured or an organism to be measured which is deposited in a free state (a state in which the material or the organism is not coupled with the receptor) on the interior of the thin-tube type solid phase 19 is washed away, and only the material to be measured or the organism to be measured which is coupled with the receptor remains in the thin tube. When the flow rate of the substrate solution in the washing operation is set to be sufficiently high, the output voltage V0 which is obtained immediately after the washing operation can be deemed as the output voltage corresponding to the pH of a fresh substrate solution.

The data processing unit 71 reads the output voltage V0 of the pH electrode 30 at the timing when the washing operation is ended, and stores the output voltage.

The drive controlling unit 72 then stops the solution feed pump 40 for a predetermined time period. During this period, in the thin-tube type solid phase 19, the reaction between the substrate and the captured material or organism which can induce a pH-change of substrate solution proceeds. As a result of the reaction, the substrate in the substrate solution is decomposed and the pH of the substrate solution in the thin-tube type solid phase 19 becomes changed.

Thereafter, the drive controlling unit 72 controls the solution feed pump 40 to slightly rotate in the rearward direction so that the substrate solution reversely flows, and then stops the solution feed pump 40. As a result, the substrate solution in the thin-tube type solid phase 19 which solution has undergone the reaction reaches the pH electrode sensing portion accommodating portion 21. In accordance with this movement, the output voltage of the pH electrode 30 is varied. When a predetermined time period elapses after the stop of the solution feed pump 40, the data processing unit 71 reads and stores the output voltage V of the pH electrode 30. This voltage corresponds to the pH of the substrate solution after the reaction. The data processing unit 71 calculates the following expression by using the stored data V0 and V to obtain a pH-change of the substrate solution due to the material which can induce a pH-change of substrate solution or the organism which can induce a pH-change of substrate solution. The obtained value is displayed on the display unit 18.

$$\Delta pH = (V - V0)/S \quad (1)$$

where S is the sensitivity of the pH electrode 30. The value of $\Delta pH$ is increased (in the case of minus, decreased) as the measuring object, or the concentration of the material or the organism which can induce a pH-change of substrate solution, in the substrate solution is increased.

Next, the operator takes out the thin-tube type solid phase 19 from the measurement cell 1 and instructs the drive controlling unit 72 to rotate the solution feed pump 40 in the forward rotation. As a result, the interior of the measurement cell 1 is washed by the substrate solution.

In order to illustrate the invention more specifically, test examples will be described.

Test Example 1

A. Configuration of an Apparatus

The apparatus is fundamentally configured in the same manner as that shown in FIG. 1. A pH-FET which is disclosed in Japanese patent publication (Kokoku) No. HEI4-51786 and in which a pH sensitive membrane is made of tantalum oxide was used as the pH electrode 30. The pH electrode has the following dimensions, i.e., the width of 0.45 mm, the thickness of 0.2 mm, and the length of 5.5 mm. A tip end portion of 0.8 mm in the pH electrode serves as the pH electrode sensing portion 6. In the pH-FET, a tip end portion of about 2 mm was exposed, and the reaming portion was embedded into a resin member of an outer diameter of 0.60 mm, together with lead wires for the source and the drain bonded to the device, thereby constituting a pH electrode body portion 4. The pH electrode had a pH sensitivity of 58 mV/pH at 25° C., and a mutual conductance of 350 microsiemens.

A silver wire the surface of which is chlorinated was used as the reference electrode 12. The pH electrode 30 was positioned so that the pH electrode sensing portion 6 was accommodated in the accommodating portion 21 (having an inner diameter of 0.7 mm), and the reference electrode was 12 was accommodated in the portion filled with fresh substrate solution 3. These electrodes were fixed to the pH electrode connector 13. At this time, the pH electrode 30 was positioned so that the distance between the upper end of the pH electrode 30 and the lower end of the thin-tube type solid phase 19 is in the range of about 0.1 to 2.0 mm. The pH electrode 30 (pH-FET) was operated at the drain voltage of 3 volts and the drain current of 7 $\mu$A and with connecting the electrode to a constant current circuit. The source potential of the pH electrode 30 relative to the reference electrode 12 was measured as the output signal of the pH electrode 30 (pH-FET).

A tube pump which is driven by a stepping motor was used as the solution feed pump 40.

The electric circuit unit 70 comprises a digital computer which is provided with functions of controlling the solution feed pump 40, and performing a calculation process on the basis of the output signal of the pH electrode 30. These functions correspond to the drive controlling unit 72 and the data processing unit 71 shown in FIG. 1, respectively.

B. Preparation of the Thin-tube Type Solid Phase 19

As the receptor, used was a monoclonal antibody to urease secreted by Helicobacter pylori (see K. Nagata, T. Mizuta, Y. Tonokatsu et al., Infection and Immunity 60, 4826-31 (1992)). Twenty thin tubes made of polypropylene (the inner diameter: 0.60 mm, the outer diameter: 1 mm, and the length: 15 mm) were soaked into 1 ml of a PBS solution (pH: 7.4) of 50 $\mu$g/ml of the monoclonal antibody, and allowed to stand at room temperature for 24 hours, thereby immobilizing the antibody to the inner and outer faces of the thin tube.

Next, the antibody solution was separated by centrifugal separation. The thin tubes were soaked in a PBS solution (pH: 7.4) containing 10% of saccharose, 1% of bovine serum albumin, and 0.1% of sodium azide, and allowed to stand at room temperature for 24 hours, whereby a blocking treatment was carried out. Thereafter, the blocking solution was separated by centrifugal separation. The thin-tube type solid phases were air-dried at room temperature. The thin-tube type solid phases were then accommodated in a hermetically sealed container and kept at 4° C.

C. Measurement of Urease Secreted by Helicobacter Pylori

Urease secreted by Helicobacter pylori (see the above-identified publication by K. Nagata et al.) was diluted with a PBS solution (pH: 7.4) to prepare plural kinds of sample solutions of different predetermined concentrations. The thin-tube type solid phases 19 which were prepared in B above were soaked into the sample solutions of 10 $\mu$l, respectively and allowed to stand at room temperature for 1 hour.

As the substrate solution, an aqueous solution containing 2 mM of urea, 10 mM of ammonium chloride, and 154 mM of sodium chloride was used.

The operator instructs the electric circuit unit 70 to start the operation. While supplying the substrate solution at a flow rate of 3 ml/min. to the measurement cell 1 by the solution feed pump 40, the operator inserts the thin-tube type solid phases 19 taken out from one of the sample solutions, into the thin-tube type solid phase insertion portion 7 of the measurement cell 1. The supply of the substrate solution is conducted for 60 seconds after the start, and the interior of the thin-tube type solid phase 19 is washed. After the time period of 60 seconds elapses, the drive controlling unit 72 stops the solution feed pump 40. At the same time, the data processing unit 71 reads and stores the output voltage V0 of the pH electrode 30 at this timing.

Thereafter, the drive controlling unit 72 keeps the solution feed pump 40 stopping for 55 seconds so that the decomposition reaction of the substrate proceeds in the thin-tube type solid phase 19. Thereafter, the solution feed pump 40 is rotated by 2 steps in the rearward direction and then stopped. The step number in the rearward direction corresponds to the reverse flow of about 1 μl of the substrate solution in the thin-tube type solid phase 19. The data processing unit 71 reads and stores the source potential V of the pH electrode 30 at a timing when a time period of 5 seconds elapses after the rotation in the rearward direction, and calculates above expression (1) on the basis of this potential V and the previously stored potential V0, to obtain ΔpH. The obtained ΔpH is displayed on the display unit 18.

Next, the operator takes out the thin-tube type solid phase 19 from the measurement cell 1, and then instructs the data processing unit 71 to rotate the solution feed pump 40 in the forward direction so that the substrate solution is supplied at a flow rate of 3 ml/min. to the measurement cell 1 for 15 seconds, thereby washing the interior of the measurement cell 1.

The operator conducted the above-mentioned operations on all of the thin-tube type solid phases 19 respectively soaked in the sample solutions. The results are shown by void squares in FIG. 3.

Test Example 2

A. Configuration of an Apparatus

The apparatus was configured in the same manner as that of A of test example 1.

B. Preparation of the Thin-tube Type Solid Phase

Thin-tube type solid phases wherein glass wool to which an antibody was immobilized was filled into a thin tube were prepared in the following manner.

In 1 ml of an antibody solution which is identical with that described in test example 1, 0.2 g of glass wool was soaked, and then allowed to stand at room temperature for 24 hours. The antibody solution was separated by centrifugal separation. Thereafter, the glass wool was soaked in 1 ml of a blocking solution which is identical with that of test example 1, for 24 hours to conduct a blocking treatment. The blocking solution was separated by centrifugal separation, and the glass wool was air-dried. About 5 mg of the glass wool was uniformly filled in each of thin tubes (to which an antibody is not immobilized) which are identical with those used in test example 1. The resulting products were used as thin-tube type solid phases.

C. Measurement of Urease Secreted by Helicobacter Pylori

The measurement was conducted in the same manner as C of test example 1. The measurement results are shown by solid circles in FIG. 3.

Comparison Example

In order to compare the apparatus of the invention with an apparatus of the prior art, the following test was conducted.

A. Configuration of an Apparatus

The apparatus was configured by using parts which are identical with those used in A of test example 1 except that the position of the pH electrode 30 was slightly upward shifted so that the pH electrode sensing portion 6 was accommodated in the thin-tube type solid phase insertion portion 7.

B. Preparation of the Thin-tube Type Solid Phase

The preparation was conducted in the same manner as B of test example 1.

C. Measurement of Urease Secreted by Helicobacter Pylori

In the same manner as C of test example 1, the thin-tube type solid phase was reacted with the sample solution for 1 hour, the thin-tube type solid phase was inserted into the measurement cell while suppling the substrate solution, and the washing operation was conducted for 60 seconds. Thereafter, V0 was read. Next, the solution feed pump was stopped for 55 seconds, and the output V of the pH electrode at a timing when a time period of 55 seconds elapsed after the beginning of the stop operation was read. The thin-tube type solid phase was then taken out from the measurement cell, and the washing operation was conducted for 15 seconds. Then, ΔpH was calculated in accordance with expression (1) by using thus measured V0 and V. The measurement results are shown by void circles in FIG. 3.

Figure 3:
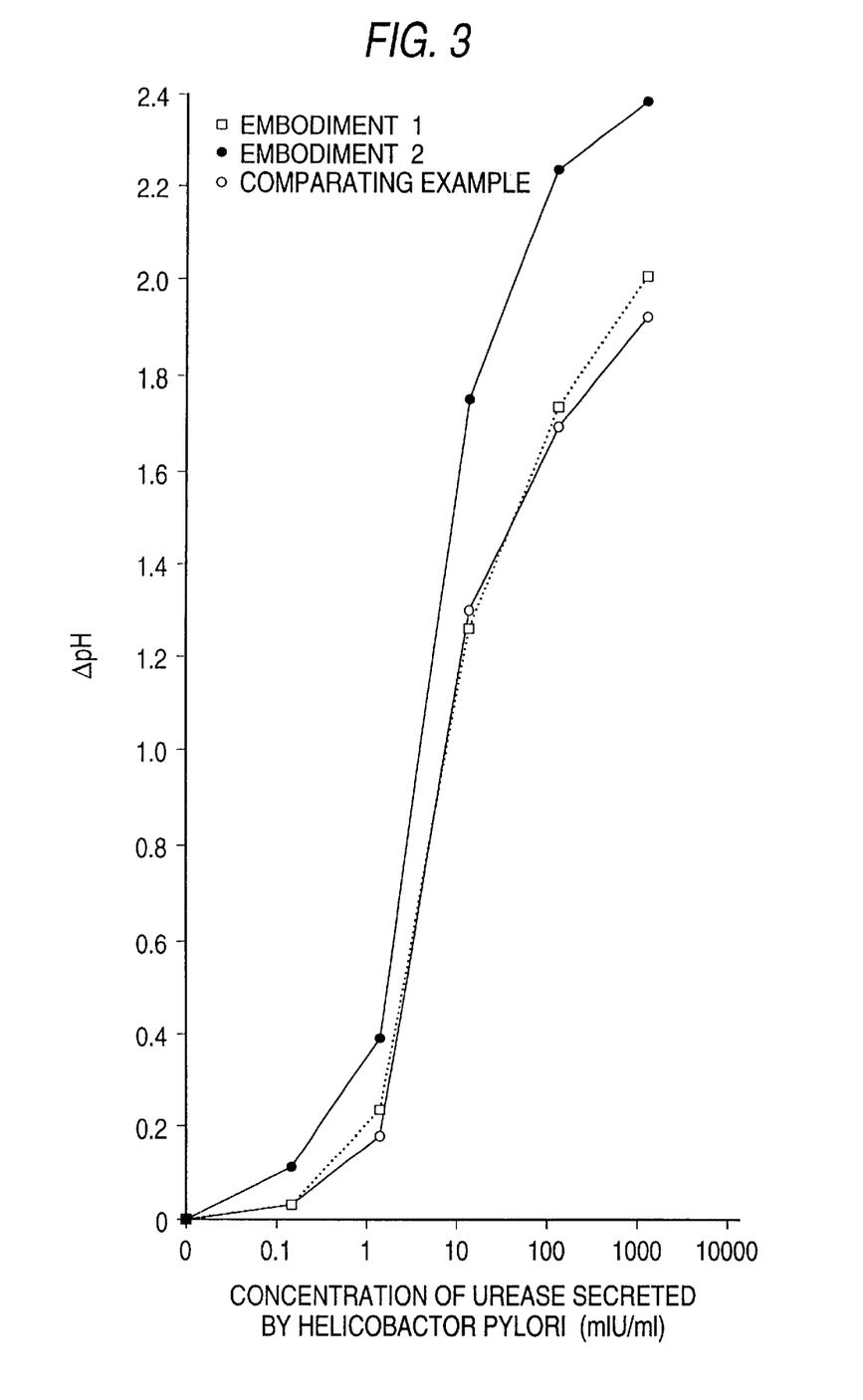
FIG. 3 is a graph showing comparisons between measurements results according to the invention and those according to the prior art.

As apparent from the results of FIG. 3, when the measurements were conducted by using identical thin-tube type solid phases, the signal strength in the measurement results according to the invention is substantially equal to those obtained in the coupling of the prior art. In other words, also in the method of the invention in which the fear that the thin-tube type solid phase is contacted with the pH electrode is completely eliminated, it is possible to obtain a signal strength which is substantially equal to that obtained in the prior art method using a coupling. According to the invention, the strength of the detection signal can be largely increased by using a thin-tube type solid phase having a larger specific surface area, such as the thin-tube type solid phase wherein a glass wool solid phase, which has been physically impossible to be used in the prior art, is filled.

According to the present invention, a material which can induce a pH-change of substrate solution or an organism which can induce a pH-change of substrate solution can be measured with a high sensitivity and a high speed and without the fear of breaking or contaminating the pH electrode.

According to the present invention, the substrate solution in the thin-tube type solid phase can reach the sensing portion of the pH electrode without being substantially diluted, and the measurement can be conducted with high accuracy. Furthermore, the invention attains an effect that the amount of the solution to be moved can be reduced, the volume of the whole of the cell can be reduced, and the required amount of the sample solution can be made smaller.

According to the present invention, the measurement of the concentration of urease secreted by Helicobacter pylori can be performed with a high sensitivity and a high speed and without the fear of breaking or contaminating the pH electrode.

The apparatus of the invention is small in size and has an excellent responsibility and a high sensitivity.

According to the present invention, the specific surface area of the thin-tube type solid phase can be increased and the detection limit can be lowered.

According to the present invention, a material which can induce a pH-change of substrate solution or an organism which can induce a pH-change of substrate solution can be measured with a high sensitivity and a high speed and without the fear of breaking or contaminating the pH electrode.

What is claimed is:

1. A measuring apparatus for a material which can induce a pH-change of substrate solution or an organism which can induce a pH-change of substrate solution, comprising:

a thin-tube type solid phase including a thin tube, with a receptor specific for the material which can induce a pH-change of substrate solution or for the organism which can induce a pH-change of substrate solution being immobilized at least to an interior of said thin tube, the material or the organism being an object to be measured;

a measuring cell accommodating a substrate solution containing a substrate for the material which can induce a pH-change of substrate solution or the organism which can induce a pH-change of substrate solution;

thin-tube type solid phase holding member for holding at least one end of said thin-tube type solid phase, in said cell;

a pH electrode having a sensing portion disposed in a pH electrode sensing portion accommodating portion which is adjacent to said thin-tube type solid phase holding member containing said one end of said thin-tube type solid phase held in said cell, said pH electrode detecting a pH change of said substrate solution; and substrate solution moving means for moving said substrate solution in said thin-tube type solid phase held in said cell, toward said sensing portion, further comprising wherein a gap is defined between a plane parallel to a tip end surface of the pH electrode and a plane parallel to an end surface of said thin-tube type solid phase, which is confronted with said plane parallel to said tip end surface.

2. A measuring apparatus for a material or an organism which can induce a pH-change of substrate solution according to claim 1, wherein, in said cell, a volume of a space between a basal end of said sensing portion of said pH electrode and said one end of said thin-tube type solid phase excluding a volume occupied by said sensing portion is 10 microliters or less.

3. A measuring apparatus for a material or an organism which can induce a pH-change of substrate solution according to claim 1, wherein said receptor is an antibody to Helicobacter pylori urease, and said substrate solution comprises urea.

4. A measuring apparatus for a material or an organism which can induce a pH-change of substrate solution according to claim 1, wherein said pH electrode is a pH sensitive field effect transistor.

5. A measuring apparatus for a material or an organism which can induce a pH-change of substrate solution according to claim 1, wherein a fibrous material is disposed in at least a part of said interior of said thin tube, and further wherein the receptor specific for a material which can induce a pH-change of substrate solution or an organism which can induce a pH-change of substrate solution is immobilized in said fibrous material, the material or the organism being an object to be measured.

6. A method for measuring or an organism which can induce a pH-change of substrate solution comprising:

soaking one end of a thin-tube type solid phase in a sample solution and taking out from said sample solution, so that said thin-tube type solid phase includes a receptor specific for a material which can induce a pH-change of substrate solution or an organism which can induce a pH-change of substrate solution, said receptor being immobilized at least to an interior of a thin tube, the material or the organism being an object to be measured;

disposing said one end of said thin-tube type solid phase in a substrate solution and in a first space in the vicinity of a sensing portion of a pH electrode for detecting a pH-change of said solution, said substrate solution containing a substrate for the material which can induce a pH-change of a substrate solution or the organism which can induce a pH-change of substrate solution, wherein a gap is defined between a plane parallel to a tip end surface of the pH electrode and a plane parallel to an end surface of said thin-tube type solid phase, which is confronted with said plane parallel to said tip end surface; and moving said substrate solution from within said thin-tube type solid phase to said sensing portion of said pH electrode, after a reaction of induction of a pH-change of said substrate solution, to thereby measure said material or said organism.

7. A measuring apparatus for a material or an organism which can induce a pH-change of substrate solution according to claim 1, wherein said substrate solution moving means comprises a stepping motor which causes said substrate solution to alternately flow in a forward and reverse direction.

8. A measuring apparatus for a material or an organism which can induce a pH-change of substrate solution according to claim 1, wherein said thin-tube type solid phase has a diameter which is larger than a diameter of said electrode sensing portion accommodating member, so that said thin-tube type solid phase does not enter into said electrode sensing portion accommodating portion.

9. A measuring apparatus for a material which can induce a pH-change of substrate solution or an organism which can induce a pH-change of substrate solution, comprising:

a thin-tube type solid phase including a thin tube, wherein a fibrous material is disposed in at least a part of an interior of said -thin-tube, and further wherein a receptor specific for the material which can induce a pH-change of substrate solution or for the organism which can induce a pH-change of substrate solution is immobilized in said fibrous material, the material or the organism being an object to be measured;

a measuring cell accommodating a substrate solution containing a substrate for the material which can induce a pH-change of substrate solution or the organism which can induce a pH-change of substrate solution;

thin-tube type solid phase holding member for holding at least one end of said thin-tube type solid phase, in said cell;

a pH electrode having a sensing portion disposed in a pH electrode sensing portion accommodating portion which is adjacent to said thin-tube type solid phase holding member containing said one end of said thin-tube type solid phase held in said cell, said pH electrode detecting a pH change of said substrate solution; and substrate solution moving means for moving said substrate solution in said thin-tube type solid phase held in said cell, toward said sensing portion;

wherein a gap is defined between a plane parallel to a tip end surface of the pH electrode and a plane parallel to an end surface of said thin-tube type solid phase, which is confronted with said plane parallel to said tip end surface.

* * * * *